United States Patent
Von Guttenberg et al.

(10) Patent No.: US 12,134,780 B2
(45) Date of Patent: Nov. 5, 2024

(54) METHOD FOR THE CULTURING OF CELLS

(71) Applicant: ibidi GmbH, Gräfelfing (DE)

(72) Inventors: Zeno Von Guttenberg, Gräfelfing (DE); Britta Hagmeyer, Reutlingen (DE); Simon Werner, Reutlingen (DE); Christian Schmees, Reutlingen (DE); Michael Pawlak, Reutlingen (DE); Martin Stelzle, Reutlingen (DE)

(73) Assignee: ibidi GmbH, Graefelfing (DE)

( * ) Notice: Subject to any disclaimer, the term of this patent is extended or adjusted under 35 U.S.C. 154(b) by 279 days.

(21) Appl. No.: 17/205,700

(22) Filed: Mar. 18, 2021

(65) Prior Publication Data

US 2021/0292707 A1     Sep. 23, 2021

(30) Foreign Application Priority Data

Mar. 19, 2020 (DE) .......................... 102020107599.5

(51) Int. Cl.
*C12N 5/00* (2006.01)
*C12M 1/00* (2006.01)

(52) U.S. Cl.
CPC ........... *C12N 5/0062* (2013.01); *C12M 23/02* (2013.01); *C12M 23/50* (2013.01); *C12N 5/0068* (2013.01); *C12N 2513/00* (2013.01); *C12N 2525/00* (2013.01)

(58) Field of Classification Search
None
See application file for complete search history.

(56) References Cited

U.S. PATENT DOCUMENTS

| | | |
|---|---|---|
| 2013/0029422 A1 | 1/2013 | Goral et al. |
| 2013/0040885 A1 | 2/2013 | Takayama et al. |
| 2016/0097028 A1 | 4/2016 | Tung et al. |
| 2016/0340632 A1 | 11/2016 | Breinlinger et al. |
| 2018/0187136 A1* | 7/2018 | Lichtenberg ........... C12M 23/20 |
| 2023/0174909 A1* | 6/2023 | Zhang .................. C12N 5/0062 |
| | | 435/297.1 |

FOREIGN PATENT DOCUMENTS

| | | | |
|---|---|---|---|
| WO | WO-2013116449 A1 * | 8/2013 | ........ B01L 3/502761 |
| WO | 2015164846 A1 | 10/2015 | |
| WO | 2017161210 A1 | 9/2017 | |
| WO | 2019/121984 A1 | 6/2019 | |
| WO | 2019121162 A1 | 6/2019 | |
| WO | 2019166644 A1 | 9/2019 | |

OTHER PUBLICATIONS

Fu CY, Tseng SY, Yang SM, Hsu L, Liu CH, Chang HY. A microfluidic chip with a U-shaped microstructure array for multicellular spheroid formation, culturing and analysis. Biofabrication. Mar. 2014;6(1):015009. doi: 10.1088/1758-5082/6/1/015009. Epub Mar. 4, 2014. PMID: 24589876. (Year: 2014).*

Amcor Flexibles North America. "Parafilm® M Laboratory Film." Aug. 2019. https://f.hubspotusercontent00.net/hubfs/2176008/PDF/amcor-techdata-parafilm-m-lab.pdf (Year: 2019).*

* cited by examiner

*Primary Examiner* — Allison M Fox
*Assistant Examiner* — Alyssa G Weston
(74) *Attorney, Agent, or Firm* — Lowenstein Sandler LLP

(57) ABSTRACT

The invention refers to a method for culturing cells in a substrate in which a chamber having at least one side wall, a bottom, and a top is formed, comprising introduction of cells into the chamber, tilting of the substrate such that the cells accumulate on a side wall of the chamber, and holding the substrate in the tilted orientation such that the cells form a three-dimensional cell aggregate.

19 Claims, 9 Drawing Sheets

Figure 1A:
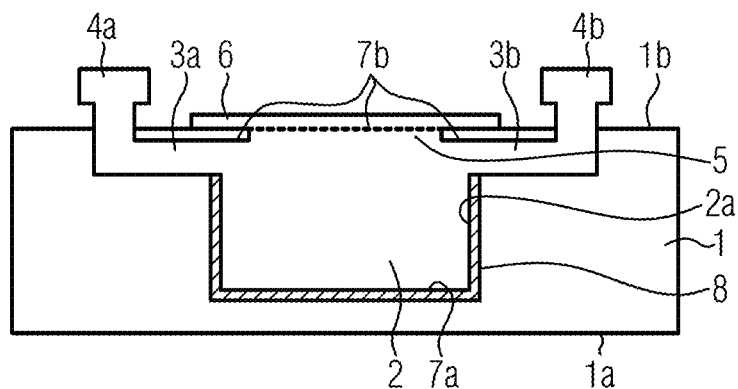

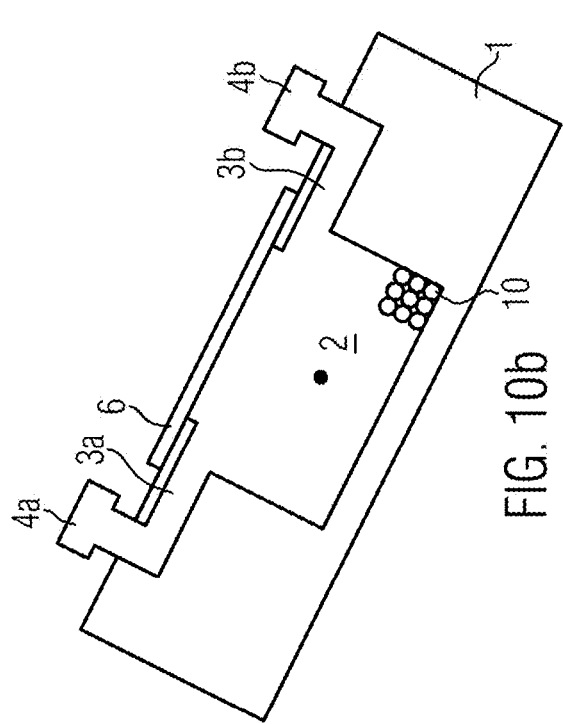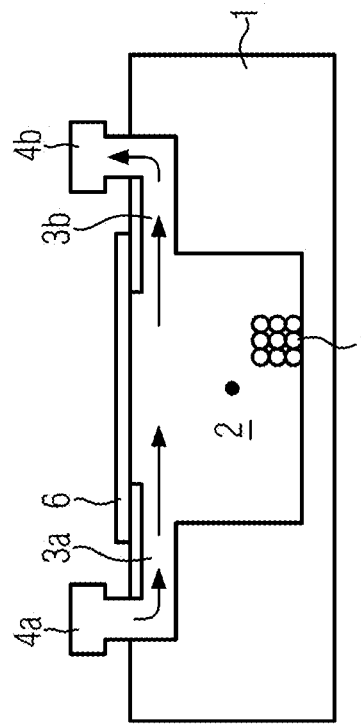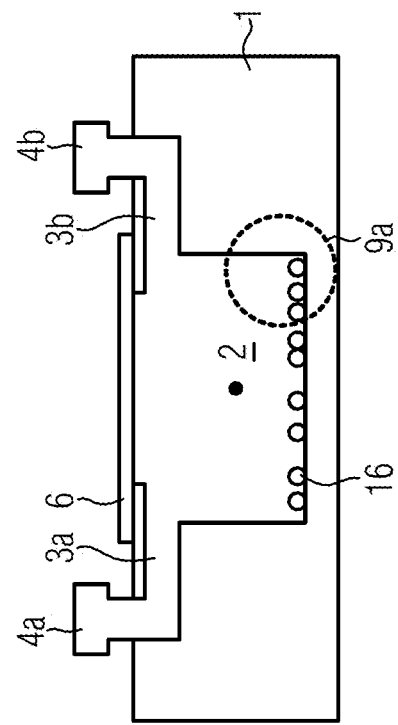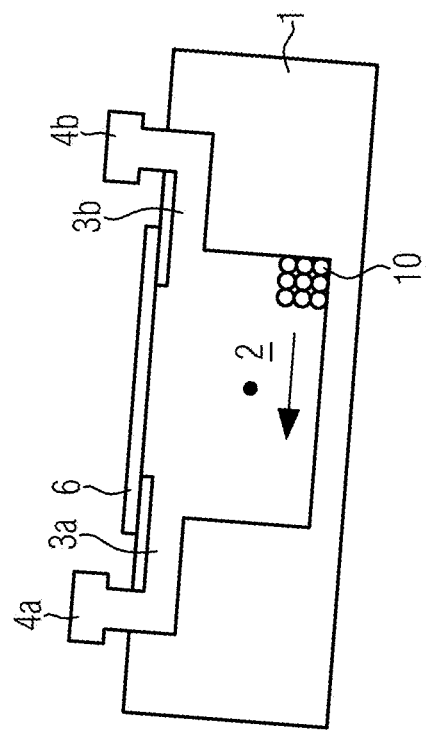
FIG. 10a
FIG. 10b
FIG. 10c
FIG. 10d

METHOD FOR THE CULTURING OF CELLS

The present application claims priority to German Patent Application No. 102020107599.5, filed Mar. 19, 2020, which is incorporated herein by reference in its entirety.

The invention refers to a method for culturing cells. The method comprises the formation of a three-dimensional cell aggregate.

In three-dimensional cell aggregates, for example cell spheroids, individual cells adhere to each other and thus represent a group of cells that corresponds more closely to the physiological conditions (organ structures) in humans and animals than is the case for a two-dimensional cell culture in a monolayer.

Although a two-dimensional cell culture is less suitable for substance testing than a three-dimensional cell aggregate, it is used more frequently. This is due, for example, to the poorer manageability in the production and examination of three-dimensional cell aggregates.

Typical cell culture methods involve that cell aggregates are formed, subsequently perfused and examined during and/or after perfusion.

For this many known systems require at least two different platforms or substrates to be used in succession. For example, in some of these systems, single cells are assembled into a cell aggregate by first pipetting the single cells into specially adapted culture plates. These can contain, for example, funnel structures or pots with a round bottom modified with a cell-repellent coating to prevent an adhesion to the surfaces. Instead of an adhesion to the surface, there is then a build-up of cell aggregates whose shape corresponds to the shape of the pots. Alternatively, plates are used to create hanging drops, with the drops each serving as an anti-adhesive cell vessel. Alternatively, cell aggregates can be assembled in holding structures in a fluid channel, namely by water droplets in oil. For this purpose, a polymer matrix is created in the water droplets into which cells can be deposited. The oil is later washed away again. Subsequently, the assembled cell aggregates are transferred or transported to separate perfusion and/or examination regions, which allow separate perfusion and/or examination of the cell aggregates.

Such a transfer or transport is laborious and can have a negative effect on the quality of the cell aggregates. Such methods are also very limited in terms of the shape of the cell culture, because the possible shape of the cell aggregates is limited to drop or pot shape.

Although other systems allow to avoid such a transfer or transport of cell aggregates, as described for example in US 2016/097028 A1. In this system, a microfluidic channel with square recesses at the bottom of the channel is used, in which three-dimensional cell cultures are formed. The shape of the cell cultures substantially corresponds to the shape of the recess. The cell cultures can be perfused and examined by microscopy. The disadvantage of this system is that there is little flexibility in terms of the shape of the recesses if the cell cultures are to be of a particular shape and size. Accordingly, the recesses can only be adapted to a limited extent to requirements for the perfusion, for example with regard to the flow behavior, or to requirements for optical examinations.

It is an object of the invention to provide a method, a substrate, and a system for culturing cells that enable three-dimensional cell aggregates to be obtained in a simple manner, with few restrictions on the shape of the perfusion and examination region.

The method according to the invention for culturing cells in a substrate in which a chamber having at least one side wall, a, in particular planar, bottom and a top is formed, comprises the introduction of cells into the chamber, tilting the substrate to a tilted orientation such that the cells accumulate on a side wall of the chamber, holding the substrate in the tilted orientation such that the cells form a three-dimensional cell aggregate.

The method is simple and requires little effort, and different shapes of cell aggregates can be easily produced, which will be explained in more detail below. Thus, the flexibility in terms of the aggregate shape is also high. The shape, in particular also bottom shape, and the size of the chamber are not further limited, so that also thereby high flexibility is possible with respect to optical examinations and perfusion. In particular, the method allows the formation of a cell aggregate and the subsequent perfusion and examination to be performed in the same chamber, so that extensive transfer steps can be dispensed with.

The accumulation on a side wall can include cells accumulating on only a single side wall or on an edge between two side walls. This can be influenced by the tilt direction.

The chamber can be a culturing and/or observation chamber, particularly an observation chamber for microscopic examinations. The chamber can be considered as a cavity formed in the substrate, said cavity being limited by the bottom and the side wall or side walls and the lid, each formed by the substrate.

The formation of a cell aggregate is also called "assembling". That a cell aggregate forms includes that the cells grow together. In particular, the formation of the cell aggregate can comprise that the cells grow together approximately in the arrangement in which they have accumulated.

For example, the cell aggregate can be spherical. Exemplarily, the spherical cell aggregate can have a diameter of about 100 to 650, in particular 150 to 600, in particular 200 to 550, in particular 250 to 500 micrometers. For example, the spherical cell aggregate can have 3000 to 7000, in particular 4000 to 6000, in particular 4500 to 5500 cells, in particular about 5000 cells. In particular, the cell aggregate can be spherical, have a diameter of 250 to 500 micrometers and have 4500 to 5500, in particular about 5000 cells.

The cell aggregate can alternatively be rod-shaped, for example. The rod-shaped cell aggregate can have a diameter of about 100 to 650, in particular 150 to 600, in particular 200 to 550, in particular 250 to 500 micrometers, and a length greater than the diameter. In particular, the rod-shaped cell aggregate can have a length of 700 micrometers to 5 mm, in particular 1 mm to 4.8 mm, in particular a length of 1.5 mm to 4.6 mm, in particular 2 mm to 4.4 mm, in particular 2.5 mm to 4.2 mm, in particular 3 mm to 4.1 mm, in particular 3.5 mm to 4 mm, in particular about 4 mm. The rod-shaped cell aggregate can have, for example, between 3000 and 45000 cells, in particular between 5000 and 40000. The rod-shaped cell aggregate can In particular, the cell aggregate can be between 3.5 and 4 mm long, have a diameter of 250 and 500 micrometers and contain between 35000 and 40000 cells.

The method for culturing cells in a three-dimensional cell aggregate can include the assembling and culturing of a three-dimensional cell culture. Such methods are also referred to as 3D cell culture. In particular, this is a so-called dynamic 3D cell culture in which the assembling and perfusion are combined in one platform.

The substrate can have a fluid structure, in particular a microfluid structure. It can be considered as a microfluidic platform. In particular, the substrate can be one of the substrates described below. In particular, the chamber can be configured as described below in connection with the substrates according to the invention.

The cells can be, for example, tumor cells or cells involved in the structure of organs, bones, tendons and cartilage.

The introduction of cells into the chamber can comprise introducing a cell suspension into the substrate through a fluid connection and transporting it into the chamber through a fluid channel, for example by means of a pump or by tilting the substrate. Alternatively, the introduction can comprise a pipetting directly into the chamber. The fluid connection can be located on the top surface of the substrate. The fluid connections can be Luer connectors.

The tilting of the substrate so that the cells accumulate on a side wall of the chamber can involve a tilting about the longitudinal axis or the transverse axis of the substrate, or about some other axis perpendicular to the vertical axis, such as the diagonal. The axis depends on the region of the chamber in which the cell aggregate is to be formed. For example, the tilting can cause the cells to move, such as slide, against the side wall or side walls due to gravity.

In particular, the axis and direction of rotation in which the substrate is tilted can each be an axis and direction of rotation that causes the tilting to cause the side wall or side walls of the chamber on which the cells accumulate to be positioned further down relative to the rest of the chamber.

The minimum length of time the substrate is held in the tilted orientation depends on what type of cell it is and how many cells form the cell aggregate. The duration that the substrate is held in the tilted orientation can either be chosen long enough that a cell aggregate is formed in any case for all possible scenarios. Alternatively, the minimum duration for each case can be determined empirically or semi-empirically.

The method can include a tilting back of the substrate following the formation of the cell aggregate. The tilting back of the substrate can include returning the substrate to the initial position, i.e., the position prior to the tilting. In addition, the substrate can optionally be tilted through the initial position and then returned to the initial position.

The method can comprise perfusing of the cell aggregate in the chamber, in particular during the tilting back and/or after the tilting back, wherein the tilting back comprises in particular a tilting back to an initial position from which it was tilted to the tilted orientation.

Perfusion means that liquid, in particular cell culture medium, flows past or around the cell aggregate. If the cell type used requires that the nutrient concentration in the surrounding cell medium is constantly high, a flowing around can be performed, for example. If the cell type used is sensitive to shear flow, superperfusion can be used, for example.

The substrate can comprise a plurality of chambers, and cells can be introduced into each of the chambers prior to tilting, such that by the tilting and holding of the substrate a cell aggregate simultaneously forms in each of the chambers. The method can then comprise perfusion of one or a plurality of the cell aggregates, in particular all of the cell aggregates, in particular independently of each other. In particular, the method can comprise a simultaneous perfusion of a plurality of, in particular all, cell aggregates.

The advantage is that a larger amount of cell aggregates can be formed under the same conditions and can be used for comparative experiments, for example, or can provide statistically better results.

The substrate can be tilted from an arrangement in which the bottom of the chamber is arranged substantially horizontally by an angle of 20° to 45°, in particular 30° to 40° . . . .

In particular, the substrate can be tilted at least far enough for the cells to collect on a side wall of the chamber. For example, the substrate can be tilted at most far enough that the cells cannot exit the chamber, particularly into a fluid channel opening into the chamber. In particular, the substrate can be tilted to the extent that the cells collect in a region of the chamber, i.e., where the side wall and the bottom meet.

The holding of the substrate can be a holding for several hours, in particular 4 to 26, in particular 6 to 25, in particular 8 to 24, in particular 10 to 23, in particular 12 to 22, in particular 14 to 21, in particular 16 to 20, in particular 17 to 19, in particular 18 hours. As seen above, the duration of the holding can be an empirically or semi-empirically determined duration for the particular application or can be at least a minimum duration at which cell aggregates are formed regardless of the application.

During the holding, environmental parameters, for example ambient temperature and/or humidity, can be monitored and, if necessary, adjusted, in particular controlled or regulated. In particular, suitable conditions can thus be created for the formation of the cell aggregate.

The method can include perfusion of the cell aggregate, as seen above.

The perfusion can comprise transporting liquid into and/or out of the chamber by means of one or a plurality of pumps. In particular, liquid can be transported to the chamber through a fluid connection and a fluid channel and out of the chamber through another fluid channel and another fluid connection.

Alternatively or additionally, the perfusion can comprise passively transporting liquid into and/or out of the chamber, for example by means of gravity. In this case, too, liquid can be transported in particular through a fluid connection and a fluid channel towards the chamber and through a further fluid channel and a further fluid connection out of the chamber.

Each of the fluid connections can be located on the top side of the substrate.

Passive systems offer the advantage that they do not require closed structures with tubes, but can be partially open. In addition, the perfusion can be achieved in the simplest case by tilting or swiveling.

The pump can be a pressure-driven or peristaltic pump. In particular, a pump system comprising a plurality of pumps can also be used. Passive fluid transport by means of gravity can be achieved by tilting the substrate or by reservoirs filled to different heights at the fluid connections.

In particular, if the perfusion involves passively moving liquid into and/or out of the chamber, the substrate can be tilted to move the liquid. Thus, the liquid is then moved by tilting the substrate. For example, the substrate can be tilted about its transverse axis to transport liquid along its longitudinal axis.

The perfusion can include that the cellular aggregate is placed in the liquid stream or superperfusion of the cellular aggregate. When the cell aggregate is placed in the liquid stream, it is flown around by the liquid. When the superperfusion takes place, the liquid flows above the cell aggregate past this cell aggregate, for example at the top edge of the chamber. How the perfusion takes place can be adjusted, in particular, by the arrangement of the fluid channels in the substrate through which the liquid is transported into and out of the chamber, especially the arrangement of their mouths into the chamber.

A substrate can be configured for exactly one of the perfusion methods, for example, if exactly two fluid channels are provided. If both fluid channels open into the chamber at the top, the substrate is configured for superperfusion, if one of them opens into the chamber at the top and one at the bottom, or if both open into the chamber at the bottom, the cell aggregate can be flown around, but a superperfusion is not possible. If at least three fluid channels, in particular with their own fluid connection, open into the chamber, with, for example, two openings at the top and one opening at the bottom, it is possible to choose between the two possibilities by using two selected fluid channels for perfusion.

The method can include a microscopic examination of the cell aggregate or cell aggregates in the chamber, particularly through the bottom of the substrate.

The cell aggregate can be observed before, during and/or after the perfusion in the chamber. In particular, such observation can be performed when the substrate is arranged horizontally. In particular, if the substrate and the chamber have suitable characteristics, for example, if one of the substrates described below in this context is used, high-resolution microscopy can be performed. The microscopic examination can comprise an examination of the growth. The method can alternatively or additionally comprise performing a fluorescence examination to determine the vitality of cells.

In particular, substance tests can be carried out using the cell aggregates in the substrate and, in particular, a microscopic examination can be performed. If a substrate with a plurality of chambers is used, independent tests in particular can be carried out simultaneously.

When a plurality of chambers is formed in a substrate, the method can comprise separately transporting, in particular circulating, a liquid through each of the chambers during the perfusion. Thus, the method can comprise the perfusion of a plurality of cell aggregates independently, each with its own liquid. In particular, substance tests can also be carried out in this way, whereby in particular a plurality of cell aggregates can be examined simultaneously and different substance concentrations can be used for different cell aggregates and/or one or a plurality of the cell aggregates can be examined as reference samples.

The substrate can have an opening above the or each chamber, which opening is closed, in particular with a lid, for example a film, at least during the formation of the cell aggregate and optionally during the perfusion. The method can comprise removing of the cells, in particular the cell aggregate or cell aggregates, from the substrate through the opening. The opening is in particular an opening directly to the outside. For the removal, the lid is taken off and then the cells, in particular the cell aggregate or cell aggregates, are removed directly from the respective chamber through the opening. In this case, the substrate can be formed in multiple parts and comprise a bottom part, in which the bottom and the side wall or side walls are formed, and the lid, wherein the lid is detachably attached to the bottom part and, in the attached state, closes the opening and forms at least part of the top of the chamber.

The advantage is that this allows direct access to the cell aggregate so that it can be removed, for example, for further examinations, optionally also in its entirety.

The invention also refers to a system comprising a substrate in which a chamber having at least one side wall, a, bottom, and a top is formed, a tilting device on which the substrate is arranged, in particular fixed, and which is configured to tilt the substrate into a tilted orientation and to hold the substrate in the tilted orientation, and a control device which is configured to control the tilting device so that it tilts the substrate into the tilted orientation and holds the substrate in the tilted orientation. In particular, the substrate can be attached to a rotational axis of the tilting device. In particular, the control device can be configured to control the tilting device such that the tilting device tilts the substrate such that, if there are cells in the chamber, the cells accumulate on a side wall of the chamber. Alternatively or additionally, the control device can be configured to control the tilting device to hold the substrate in the tilted orientation such that, if there are cells in the chamber, the cells accumulate on a side wall of the chamber to form three-dimensional cell aggregates. In particular, the control device can control such that it holds the substrate for a predetermined time, which is in particular predetermined such that when cells are present, a cell aggregate forms during that time.

The tilting device can optionally additionally be configured for tilting back the substrate, in particular for tilting back to an initial position from which the substrate was tilted into the tilted orientation. Optionally, the tilting device can also be configured for tilting the substrate through the initial position and then to the initial position. The control device can control the tilting device such that it tilts back the substrate, particularly to the initial position. In particular, the control device can control the tilting device in such a way that it tilts back the substrate automatically after a predetermined time, which is in particular long enough for cell aggregates to form in the presence of cells during this time.

The tilting device can, for example, comprise a drive, in particular a motor. The control device can be configured to control the drive in such a way that it drives the tilting and/or tilting back of the substrate.

The system can also include one or a plurality of pumps for the transporting of the liquid into and out of the chamber. The control device can then optionally also be configured to control the pumps such that the pumps transport the liquid accordingly.

The system can be configured to perform any of the methods described above. Alternatively or additionally, the system can comprise any of the substrates described below.

The invention also refers to a substrate in which a chamber having at least one side wall, a, in particular planar, bottom, and a top, wherein a side wall or at least one of the side walls and the bottom of the chamber have a cell-repellent property, in particular have a cell-repellent coating.

The chamber can have the cell-repellent property in a region that includes a portion of the bottom and a portion of the side wall adjacent thereto, or a portion of the bottom and the edge between two side walls adjacent thereto, and which is disposed below the remaining regions of the chamber when the bottom is tilted out of a horizontal configuration about an axis disposed in the horizontal plane, particularly a longitudinal axis, a transverse axis, or a diagonal, of the substrate. The side wall can have a circular arc shape or an elliptical arc shape in the region, or the side walls of the chamber can enclose an edge, in particular a rounded edge, in this region. The region can be laterally offset from the longitudinal axis of the substrate. Alternatively or additionally, the outline of the chamber can be asymmetrical.

Due to the cell-repellent property, the cells cannot grow on to the bottom or side wall during the formation of the cell aggregate.

In relation to the volume, the size of the chamber can be at least two to three times the size of the cell aggregate to be formed. In particular, one, more, or all of the length, width, and height of the chamber can each be at least two to three times the length or width or height of the cell aggregate to be formed, or each can be at least two to three times the diameter of the cell aggregate. The dimensions of the cell aggregate to be formed depend on the number of cells, the type of cells, and the shape to be formed, for example based on the shape of the side wall or side walls in the region where the cell aggregates are to be formed. In particular, based on these parameters, the dimensions of the cell aggregate to be formed can be predicted and a chamber having one of the relative sizes described above can be used. For example, the chamber can have a height and width of 1 to 5 mm each and a height of 1 to 10 mm, in particular 1 to 8 mm, in particular 1 to 4 mm, in particular 1 to 3 mm, in particular 1 to 2.5 mm.

In particular, the chamber can have a region in which exactly one, for example circular arc-shaped or elliptical arc-shaped, side wall is arranged or in which two side walls meet at right angles or at an acute angle, the edge between the two side walls being in particular rounded. In any of the methods or systems described above, the circular arc-shaped side wall can be the side wall where the cells accumulate.

The chamber can have a plurality of regions that can be used for the accumulation of the cells. The regions can have the same shape. Alternatively, the outline of the chamber can be asymmetrical. In particular, the regions can have different shapes. If the outline of the chamber is asymmetric or the regions have different shapes, cell aggregates of different geometries can be produced when the substrate is used, depending on the tilt direction.

When the cells accumulate on a straight boundary, such as a straight side wall, they form a rod-shaped cell aggregate with a substantially rectangular base region. When the cells collect at a circular arc-shaped side wall, the resulting aggregate is rod-shaped with a semicircular base. When the cells collect at a rounded edge, the cell aggregate assumes spherical or hemispherical shape.

The shape of the cell aggregate influences the number of living cells inside the cell aggregate. In the case of a spherical cell aggregate, which is also known as a spheroid, with a diameter of 400-500 μm the core usually consists of dead cells, since not enough nutrients can diffuse there. In a rod-shaped cell aggregate, the surface-to-volume ratio is usually such that the proportion of living cells is greater there. This can be particularly advantageous for subsequent examinations outside the substrate.

The substrate can be formed in whole or in part, particularly in the region of the bottom of the chamber, from a material with refractive index>1.2 and <1.7.

The substrate can be made of a plastic, in particular a biocompatible plastic. For example, the plastic material can comprise polycarbonate, polystyrene, polyethylene, polyvinyl chloride, cyclo-olefin copolymer, cyclo-olefin polymer, or polymethyl methacrylate. The plastic can comprise an elastomer. The elastomer can comprise a silicone, particularly polydimethylsiloxane, PDMS.

The substrate, in particular the region below the bottom of the chamber, can be made of material such that microscopic examination of cell growth is possible. In particular, the birefringence of the material can be sufficiently low to allow microscopic examination and/or the auto-fluorescence of the material can be sufficiently low to allow examination with fluorescence microscopy. The auto-fluorescence, in particular, can be less than or equal to the auto-fluorescence of COC (cyclo-olefin copolymer) or COP (cyclo-olefin polymer) or a conventional cover glass. In particular, the auto-fluorescence can be less than or equal to the auto-fluorescence of a conventional cover glass, for example pure white glass of hydrolytic class 1 such as Menzel cover glass, in particular with thickness No. 1.5.

With such an optically high-quality material, microscopic examinations can be carried out in an advantageous manner. For example, the birefringence can be so low that DIC (Differential Interference Contrast) is possible. Low auto-fluorescence allows fluorescence measurements to be carried out.

The substrate can be configured in the form of a microscopy carrier.

The substrate can include a first and a second fluid channel that open into the chamber, particularly at opposite ends of the chamber, and that are each connected to a separate fluid connection. In this regard, both fluid channels can open into the upper region of the chamber, or both fluid channels can open into the lower region of the chamber, or one of the fluid channels can open into the upper region of the chamber and the other fluid channel can open into the lower region of the chamber. Each of the fluid connections can be located at the top side of the substrate.

In addition to the first and second fluid channel, the substrate can include at least a third fluid channel that opens into the chamber and is connected to a separate fluid connection. Each of the fluid connections can be located on the top side of the substrate, for example. One of the fluid channels can open into the lower region of the chamber and the other two fluid channels can open into the upper region of the chamber, wherein in particular one of the fluid channels opening into the chamber in the upper region opens into the chamber at an end opposite to the end in which the fluid channel opening into the chamber in the lower region opens into the chamber. As explained above, depending on the use of the fluid connections, flow around or superperfusion can thus occur.

One of the side walls or a section of the side wall of the chamber can enclose an obtuse angle with the bottom of the chamber, in particular the side wall or section of the side wall located between the bottom of the chamber and the mouth of a fluid channel opening into the chamber from the top. Thus, the side wall or section can be oblique or inclined. In this way, unfavorable flow conditions, for example stagnation points, at the edges and corners of the chamber can be avoided.

The chamber can have a planar bottom, which can be in particular substantially parallel to the bottom side of the substrate. Additionally, the top side of the substrate can also be substantially parallel to the bottom side of the substrate and the bottom. The top side and/or bottom side of the substrate can also be planar. A substrate with a planar bottom is suitable for examination with high resolution microscopy. This is not possible with uneven bottoms, for example with the corrugated plates with round bottoms often used for the assembly, due to optical distortions.

Figure 1B:
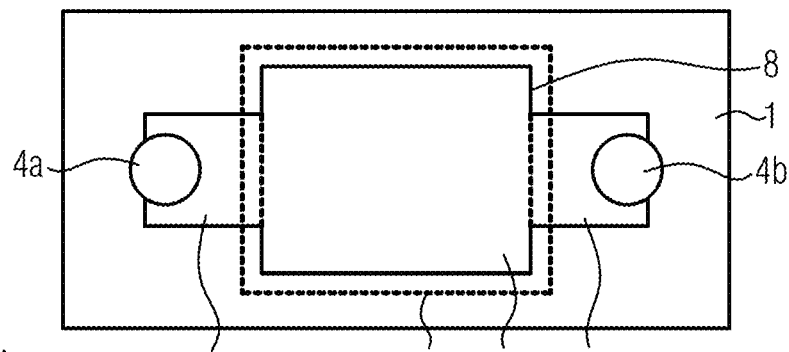
Figure 1C:
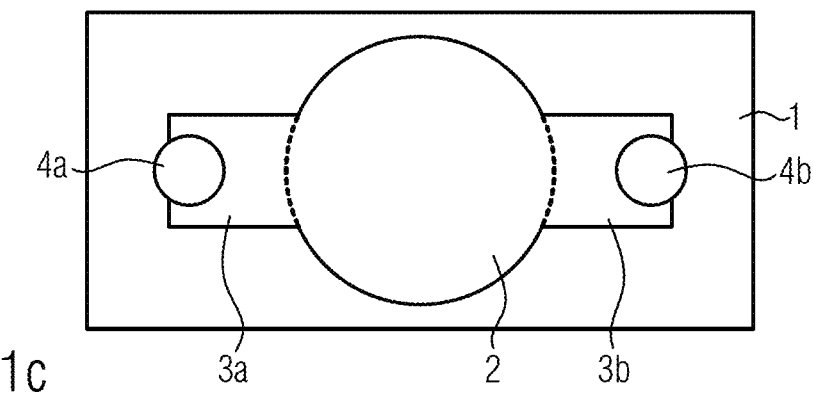
Figure 2:
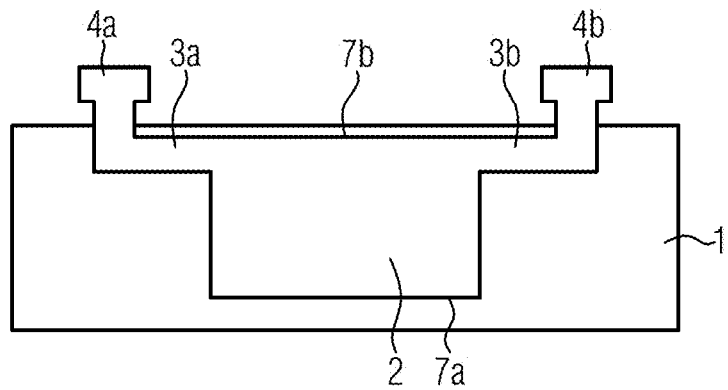
Figure 3:
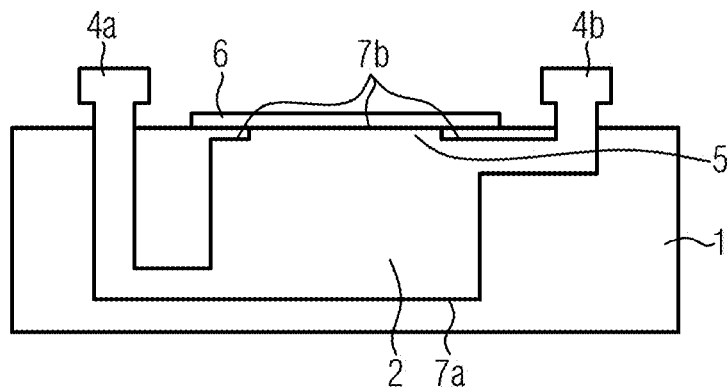
Figure 4:
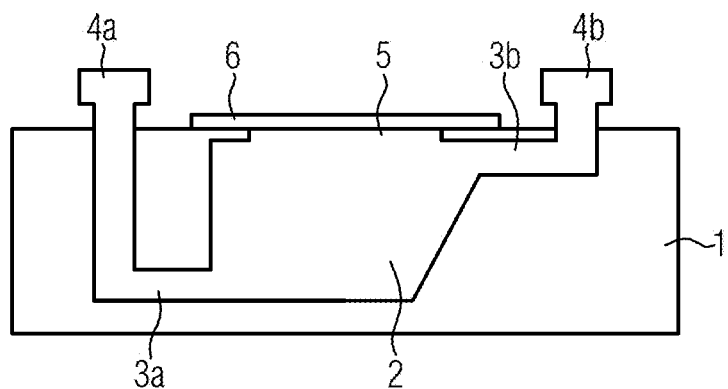
Figure 5:
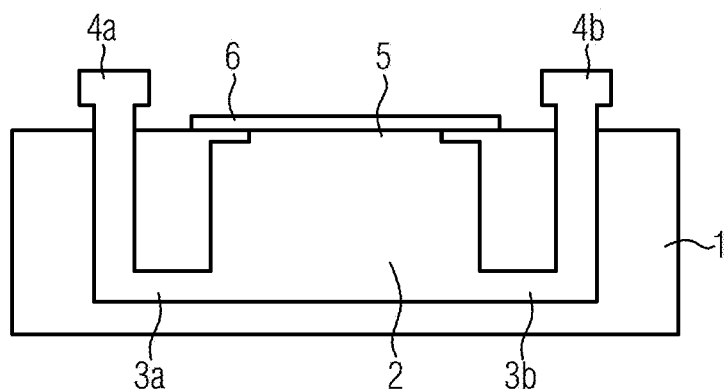
Figure 6A:
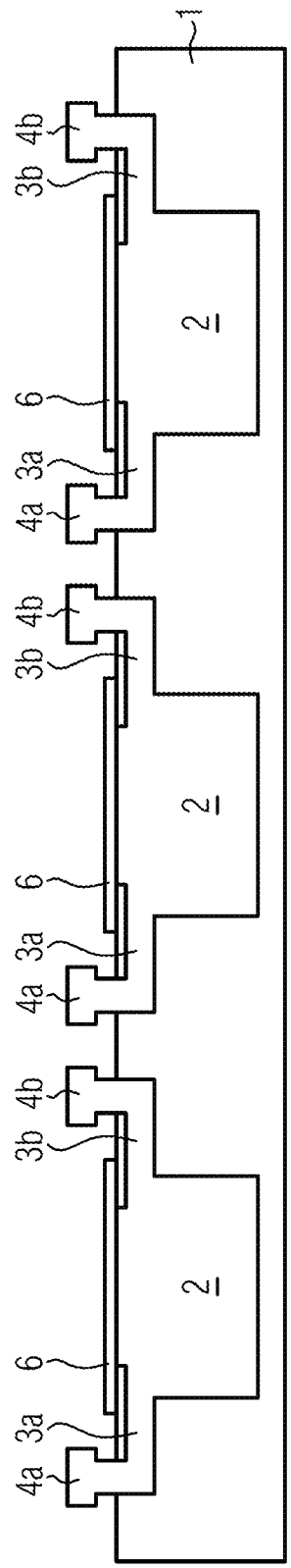
Figure 6B:
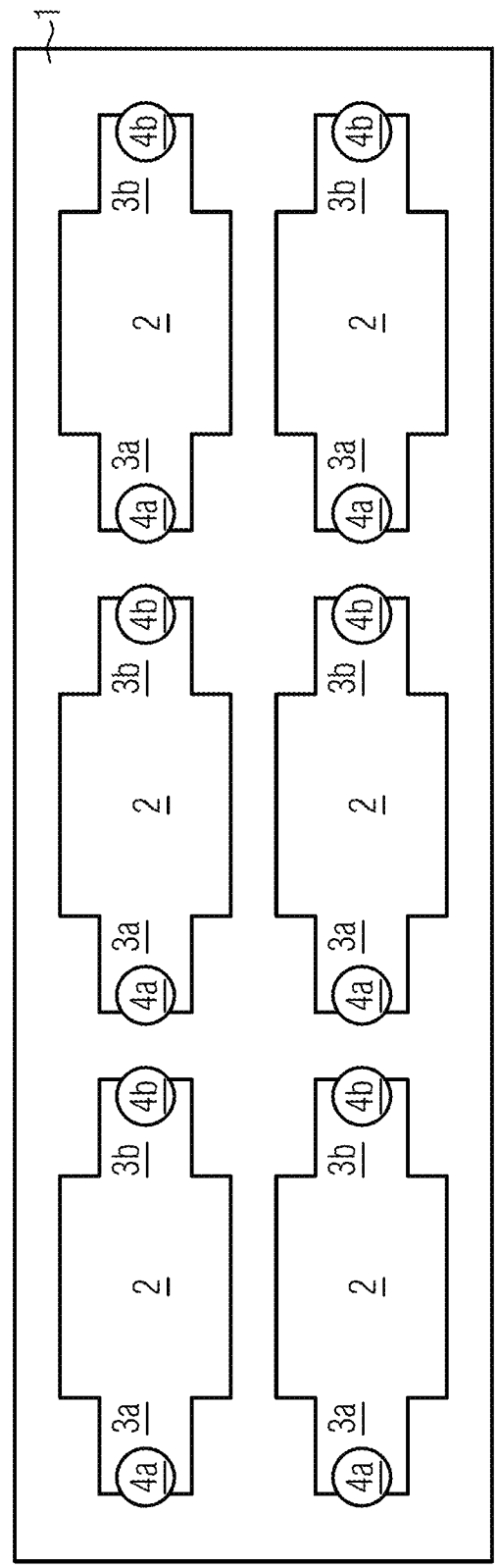
Figure 7A:
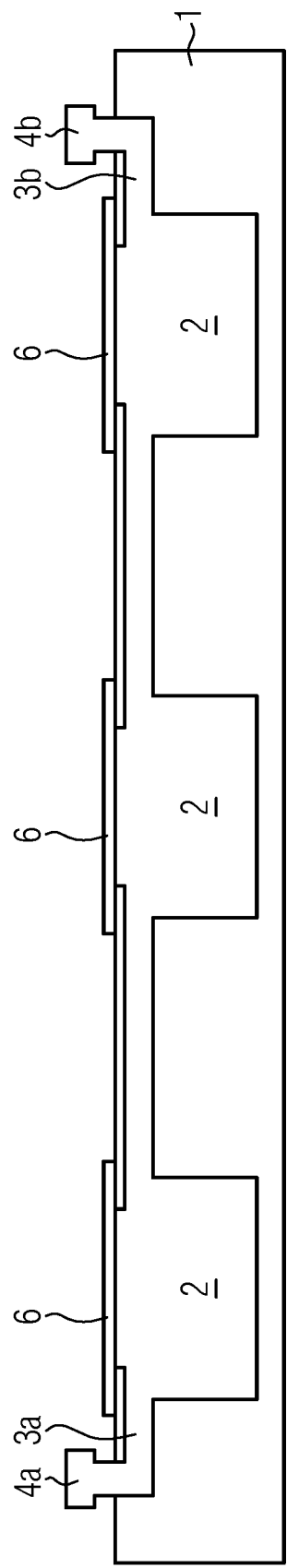
Figure 7B:
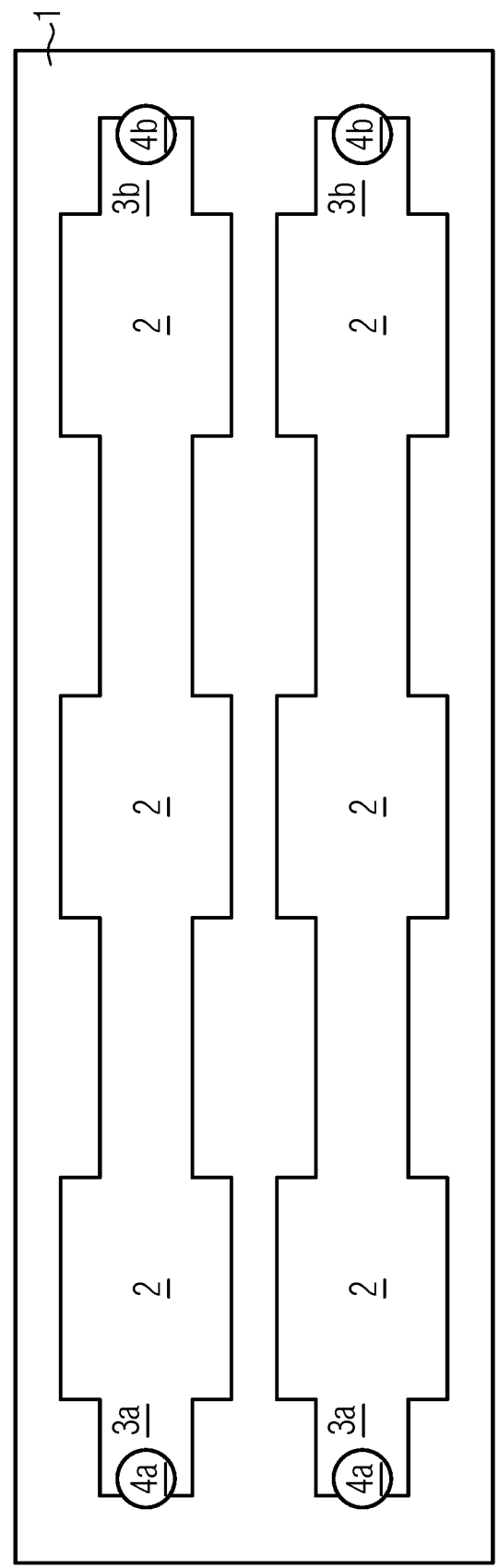
Figure 8A:
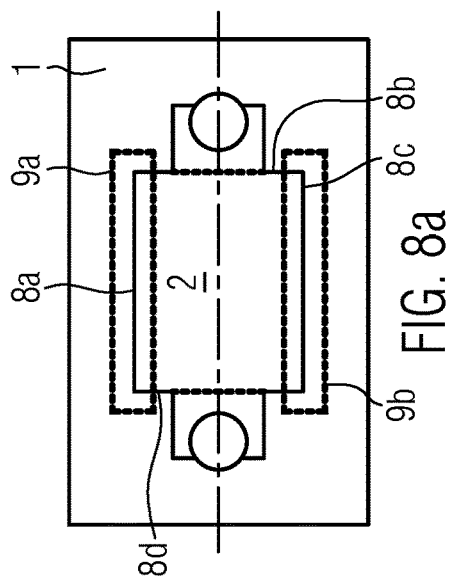
Figure 8B:
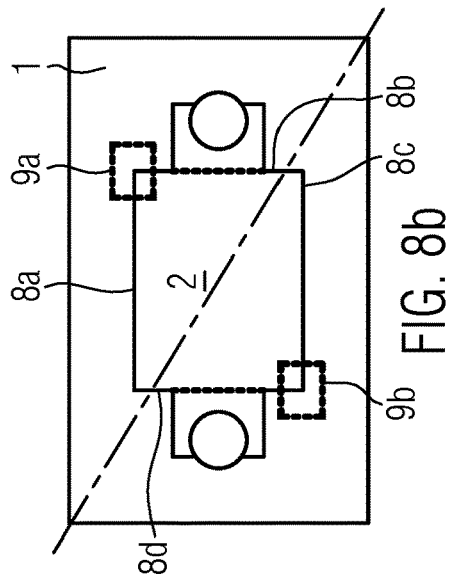
Figure 8C:
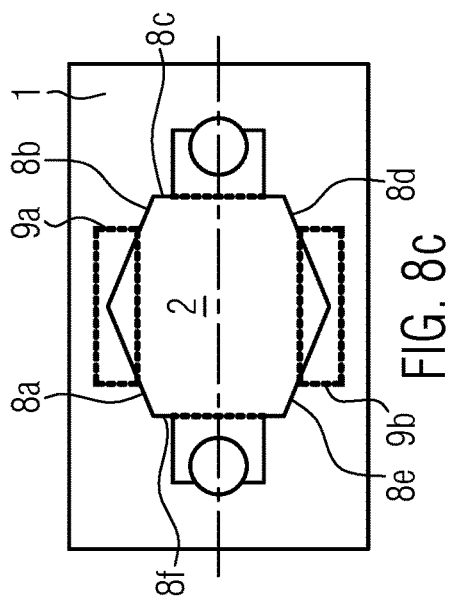
Figure 8D:
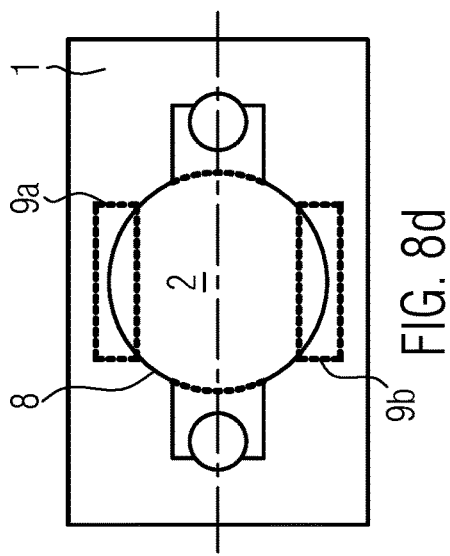
Figure 8E:
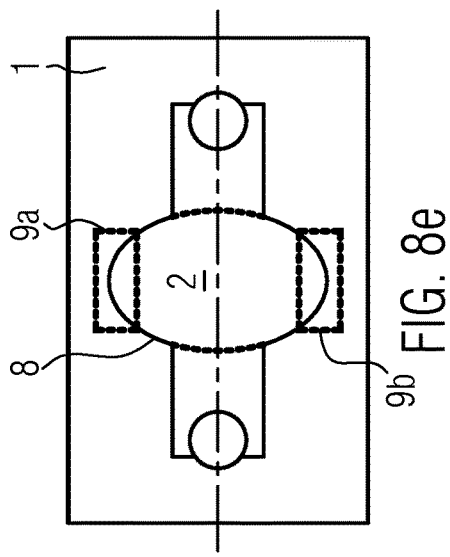
Figure 8F:
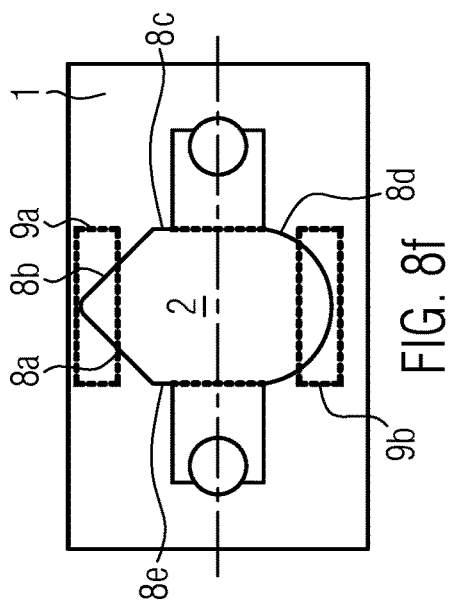
Figure 9:
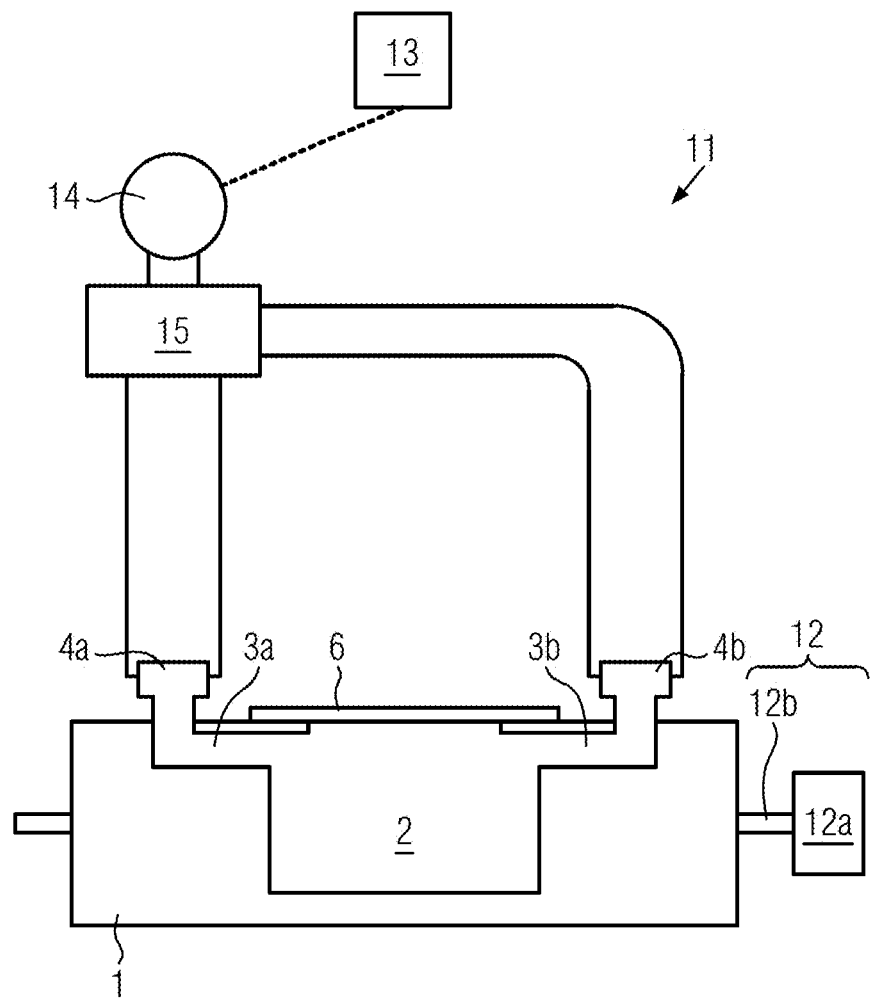

Further features and advantages are explained below with reference to the exemplary Figures:

FIGS. 1a to 1c show a schematic, not to scale side view of a substrate and top views of a substrate of a first embodiment with two alternative outlines of the chamber, FIG. 2 shows a schematic, not to scale side view of a substrate of a second embodiment, FIG. 3 shows a schematic, not to scale side view of a substrate of a third embodiment, FIG. 4 shows a schematic, not to scale side view of a substrate of a fourth embodiment, FIG. 5 shows a schematic, not to scale side view of a substrate of a fifth embodiment, FIGS. 6a and 6b show a schematic, not to scale top view of a substrate and side view of a substrate of a sixth embodiment having a plurality of chambers, FIGS. 7a and 7b show a schematic, not to scale top view of a substrate and side view of a substrate of a seventh embodiment having a plurality of chambers, FIGS. 8a to 8f show schematic, not to scale views of various outlines of the chamber, FIG. 9 shows a schematic, not to scale view of a system of an embodiment, and FIGS. 10a to 10h show a schematic view of various possible steps of a method of an embodiment.

FIG. 1a shows a side view of a substrate 1 with a chamber 2, two fluid channels 3a and 3b, and two fluid connections 4a and 4b. One end of the fluid channels opens into the chamber and the other end opens into the respective fluid connection. At least one of the fluid connections can comprise a fluid reservoir, or a fluid reservoir can be mounted on the fluid connection.

FIG. 1a shows an example of a substrate having an opening 5 above the chamber, which opening is closed with a removable lid 6, for example a film, during the formation of the cell aggregate. However, such an opening is optional.

The substrate, when having such an opening, can be formed in multiple parts and comprise a bottom part in which the bottom and side wall or side walls of the chamber are formed and the lid, the lid being removably attached to the bottom part and, when attached, closing the opening and forming at least a portion of the top of the chamber.

Alternatively, the substrate can be formed, for example, such that no openings are formed directly above the chamber. In particular, the substrate can be formed such that it has only openings directly connected to fluid connections. A substrate without the opening 5 is shown by way of example in FIG. 2, the substrate otherwise being formed as described in connection with FIG. 1.

The chamber has a bottom 7a, which is in particular planar and parallel to the bottom side 1a, which in this example is also planar, and optionally, as in this example, also parallel to the top side 1b of the substrate. The top side can also be planar, optionally apart from the fluid connections and the opening. In particular, the lid 6 can be planar. The chamber has a top 7(b).

The chamber can have different outlines, for example rectangular or round. FIG. 1b shows an example of a top view of the substrate with a rectangular outline and FIG. 1c shows a top view with a round outline.

If the substrate has a round or elliptical outline, it has a circumferential side wall 8, which can optionally be interrupted by mouths of fluid channels. If the side wall has a rectangular outline, it has four side walls 8a, 8b, 8c, 8d, which can also optionally be interrupted by mouths of fluid channels. The side wall 8 or one or a plurality of the side walls 8a to 8d, in particular all of the side walls, can be arranged substantially perpendicular to the bottom of the chamber. However, this is optional, as will be explained in detail below.

In particular, it can have any of the outlines described below in connection with FIGS. 8a to 8f. There, regions 9a and 9b of the chamber at which cells 16 located in the chamber accumulate and form a cell aggregate 10 by tilting of the substrate in a predetermined direction and by a predetermined angle are also indicated with a dashed line. In each case, the axis of rotation and direction in which the substrate is tilted for this purpose are an axis of rotation and direction that causes the tilting to cause the corresponding region of the chamber to be positioned further down relative to the rest of the chamber. Examples of how these regions of the chamber can be configured are explained below with reference to FIGS. 8a to 8f, wherein any of the configurations of the chamber shown there can be combined with the basic configuration of the substrate shown in FIG. 1a.

The wall or walls and the bottom of the chamber can have a cell-repellent property, in particular a cell-repellent coating 2a, at least in the region or regions. In particular, the entire bottom and/or the entire side wall or side walls, can have a cell-repellent property.

In particular, the substrate can be configured in the form of a microscopy carrier, especially, at least above and/or below the chamber, made of an optically high-quality material described in the general part.

In the examples shown in FIGS. 1a to 1c and 2, both fluid channels open into the upper region of the chamber. In FIG. 2, as an example, the substrate is shown without an opening above the fluid channel. Such a substrate can in particular be configured in one piece.

FIG. 3 shows a substrate that can be configured as the substrates in FIGS. 1 and 2 (i.e., with or without an opening above the chamber), with the difference that in the substrate in FIG. 3, the fluid channel 3a opens into the lower region of the chamber and the fluid channel 3b opens into the upper region of the chamber. Also in this example, the chamber can have any of the outlines described below in connection with FIGS. 8a through 8f.

Optionally, a third fluid channel can also be provided, which runs above the fluid channel 3b, in particular laterally offset from it, and opens into the upper region of the chamber. The third fluid channel can be connected to its own fluid connection. In this way, flow around or a superperfusion can optionally take place with the same substrate.

In FIG. 4, a substrate is shown that can be configured as the substrates in FIGS. 1 and 2 (i.e., with or without an opening above the chamber), with the difference that in the substrate in FIG. 4, the fluid channel 3a opens into the lower region of the chamber and the fluid channel 3b opens into the upper region of the chamber. In this example, one of the side walls or a section of the side wall of the chamber is inclined with respect to the bottom of the chamber, in particular such that the side wall and the bottom enclose an obtuse angle. In particular, in this example, the side wall or section of the side wall that is disposed between the bottom of the chamber and the mouth of the fluid channel 3b opening into the top of the chamber is inclined. Also in this example, the chamber can have any of the outlines described below in connection with FIGS. 8a through 8f, optionally with the limitation that the region where the cell aggregates are formed is not located where one of the fluid channels opens into the chamber at the bottom.

In FIG. 5, a substrate is shown which can be configured in the same way as the substrates in FIGS. 1 and 2 (i.e. with or without an opening above the chamber), with the difference that in the substrate in FIG. 5 both fluid channels 3a and 3b open into the lower region of the chamber.

FIGS. 6a and 6b show a top view and a side view of a substrate with a plurality of chambers 2. Here, all of the chambers can have the same shape or they can have different shapes. For example, each of the chambers can be configured as described above in connection with FIGS. 1 to 5. Each chamber is connected to two fluid connections 4a and 4b of its own.

Alternatively, a group of a plurality of chambers can each be connected via a fluid channel with common fluid connections. The substrate can have exactly one or a plurality of such groups. An example with two such groups is shown in FIGS. 7a and 7b in side view and top view.

FIGS. 6a, 6b, 7a and 7b show six chambers in the substrate as an example. However, this number can be varied as desired. In particular, for example, twelve or 24 chambers can be provided in the substrate and, if necessary, can be grouped as desired.

FIGS. 8a to 8f show various possible outlines of a chamber that can be used, for example, for each of the substrates described above. The chamber can have at least one side wall such as 8, 8a, 8b, 8c, 8d, 8e, or 8f. Exemplary arrangements of the fluid channels are shown in dashed lines. Exemplary tilting axes and the regions 9a and 9b resulting from tilting about this axis, in which cells accumulate, are indicated in dashed lines in the Figures.

FIG. 8a shows a chamber with a rectangular outline. FIG. 8b also shows a chamber with a rectangular outline, but here the edge between the fluid channel walls 8a and 8b is rounded. In FIG. 8c, a chamber with a polygonal outline is shown, here with six edges. In FIG. 8d, a chamber with a round outline is shown. FIG. 8e shows a chamber with an elliptical outline.

FIG. 8f shows a chamber having a first region 9a where the side walls 8a and 8b meet perpendicularly, the edge optionally being rounded as shown here. Furthermore, the chamber has a second region 9b which is opposite the first region. In this region, the side wall is in the form of an arc of a circle or ellipse. In this example, the other side walls are planar. In the present example, the planar side walls are those into which the fluid channels open.

Especially in the case of a non-rectangular and non-circular outline and/or an asymmetrical outline, a large degree of flexibility is possible with regard to the geometry of the forming cell aggregates. Depending on the direction in which the substrate is tilted, cell aggregates with different geometries can be generated.

FIG. 9 shows a system 11 with a substrate, the substrate of FIG. 1 being shown here as an example, and a tilting device 12 which is configured in such a way that it tilts the substrate, in particular automatically, and holds it in a tilted position. The tilting device can also be configured for tilting back the substrate, in particular automatically. For example, the tilting device can comprise a motor 12a that tilts the substrate and an axle 12b to which the substrate is attached and which is rotated by the motor so that the substrate is tilted. The system includes a control device 13 that controls, for example, the motor. The tilting device 12 can be configured to tilt the substrate about one or a plurality of axes.

The system can optionally also include one or a plurality of pumps 14 connected to the substrate in such a way as to be capable of pumping liquid from a reservoir 15 through the fluid connections, fluid channels, and optionally also the chamber. The pumps can be controlled by means of a control device, in particular by means of the control device 13. The pumps are not necessarily provided. Fluid transport can alternatively be accomplished by the tilting of the substrate, as explained below in connection with the method.

In the following, a method for culturing cells in a three-dimensional cell aggregate in a substrate 1 in which a chamber is formed 2 is explained with reference to FIGS. 10a to 10g. It can be carried out, for example, using one of the substrates and, where appropriate, systems described above. Other suitable substrates or systems can also be used.

The method comprises introducing cells 16 in the chamber 2. In the present example, the substrate is arranged such that the bottom of the chamber is substantially horizontal. Thereafter, the cells are distributed approximately uniformly, in particular in a monolayer, in the chamber, as shown in FIG. 10a.

The substrate is then tilted to a tilted orientation such that the cells accumulate on a side wall of the chamber. For example, the substrate can be tilted by 20° to 45°. This condition is shown in FIG. 10b. In FIG. 10b, the substrate is tilted about the transverse axis, which here is perpendicular to the drawing plane.

In the next step, the substrate is held in the tilted orientation for a predetermined period of time, such as several hours, particularly between 17 and 19 hours, especially 18 hours. The cells and the substrate are configured such that cell aggregates 10 are formed during this period. In particular, the shape of the region of the chamber where the cells accumulate determines the shape of the cell aggregates. The cell-repellent property of the side wall or side walls and the bottom of the chamber in this region allow that the cells do not grow on there. The side wall or side walls, together with the bottom, form a boundary for the cell aggregate and thus influence the shape in which the cell aggregate grows. Due to, among other things, gravity and/or surface tension, as well as growth characteristics of the cells, it is not necessary to limit the cell aggregate from all sides in order to obtain the desired shape.

Optionally, the substrate is then tilted back. Due to gravity and possibly the surface characteristics of the chamber, the cell aggregate 10 moves away from the side wall or side walls toward the center of the chamber, as shown in FIG. 10c. Optionally, the substrate can be tilted further through the initial position and then tilted back to the initial position (not shown here).

A perfusion of the cell aggregate can be performed in the chamber. For this purpose, liquid, for example cell culture medium, is introduced into the substrate through a first fluid connection 4a and a first fluid channel 3a and is discharged from the substrate through a second fluid channel 3b and a second fluid connection 4b.

Figure 10E:
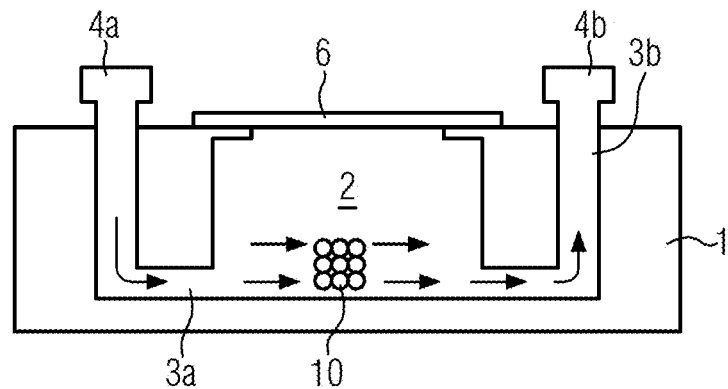

When flowing through the substrate, the liquid can only flow along the edge of the chamber, as shown in FIG. 10d. This is the case, for example, when the two fluid channels open into the chamber in the upper region of the chamber. In this case, a superperfusion occurs, i.e., the liquid does not flow around the cell aggregate but flows past it above. Alternatively, the liquid can flow around the cell aggregate, as shown in FIG. 10e, for example, when one or both fluid channels open into the chamber at the bottom.

The perfusion can be performed after the tilting back. Alternatively, the perfusion can already be performed during the tilting back.

The method is described above using a substrate in which one chamber is formed. If a substrate with a plurality of chambers is used, for example as shown in FIGS. 6a, 6b, 7a, 7b, a plurality of cell aggregates can also be formed simultaneously by introducing cells into a plurality of chambers.

The perfusion can then also be performed for a plurality of cell aggregates, in particular simultaneously. The perfusion of the individual cell aggregates can be performed independently for all cell aggregates if each chamber is connected to two separate fluid connections, for example as shown in FIGS. 6a and 6b. For this purpose, liquid is transported into the chamber via one of the two fluid connections for each of the chambers.

Alternatively, liquid can be supplied to a group with a plurality of chambers via a split fluid connection, for example with a substrate as shown in FIGS. 7a and 7b. In this way, a uniform perfusion of the cell aggregates within a group can be achieved. The substrate can have a plurality of such groups. Then, for example, a perfusion with liquid in a different composition can be performed for cell aggregates of different groups.

In particular, when using a substrate with a plurality of chambers, as shown for example in FIGS. 6a, 6b, 7a and 7b, parallel independent substance measurements can also be performed in this way.

Figure 10F:
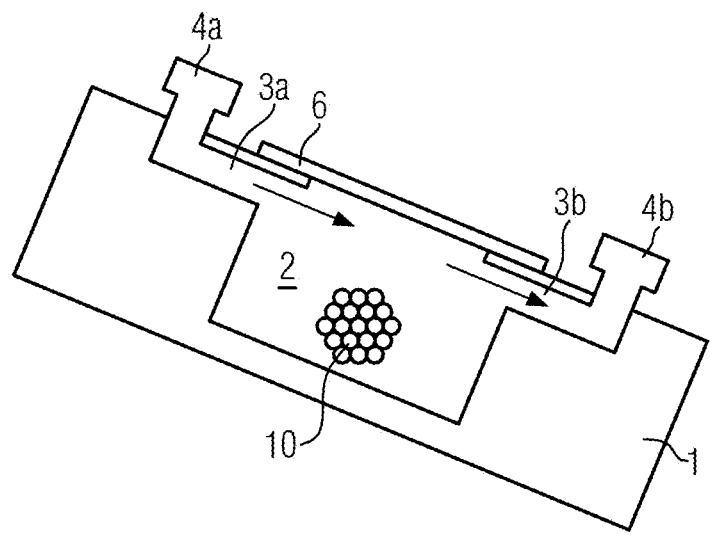
Figure 10G:
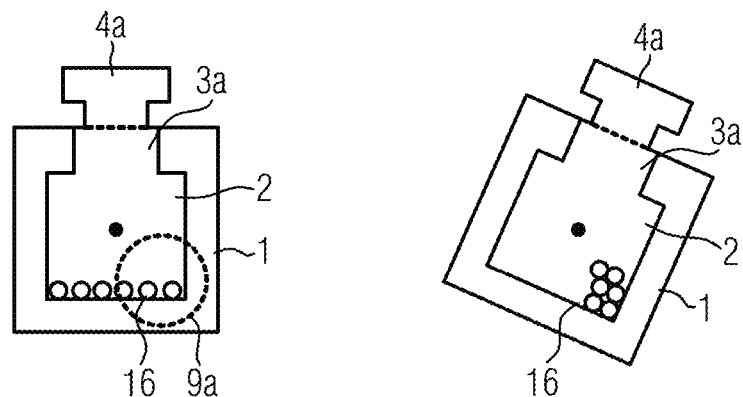
Figure 10H:
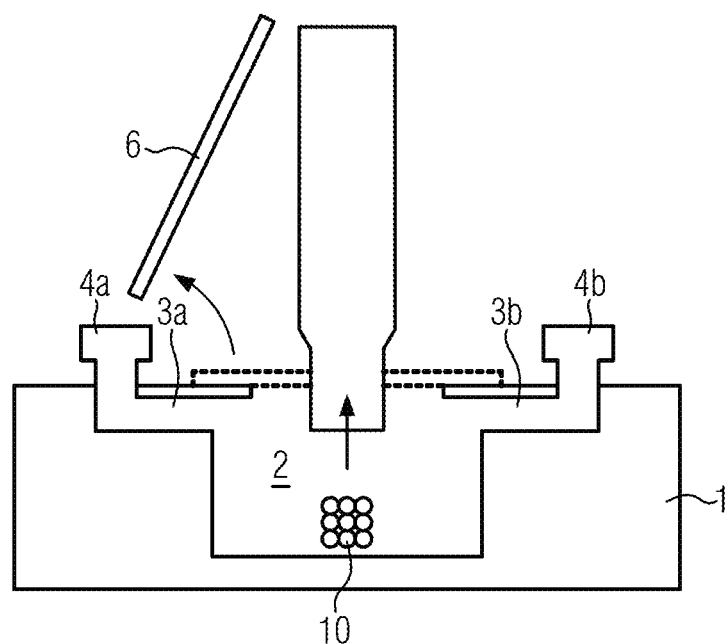

The perfusion can be accomplished by means of one or a plurality of pumps, such as in a system as shown in FIG. 9. Alternatively, the perfusion can be accomplished by the tilting of the substrate due to gravity, as shown in FIG. 10f. For example, the substrate can be tilted alternately in opposite directions to obtain flow.

In FIG. 10b, the substrate is tilted about the transverse axis. Alternatively, it can also be tilted about the longitudinal axis. In particular, if the regions used to form the cell aggregates are offset from the longitudinal axis in the transverse direction. Alternatively or additionally, the substrate can be tilted about other axes, for example one of the diagonals.

The method can optionally comprise performing a microscopic examination of the cell aggregate or cell aggregates in the chamber, particularly through the bottom of the substrate. In particular, a high resolution microscopy method can be performed, especially when the bottom of the chamber is planar. This examination is preferably performed when the substrate is oriented horizontally. It can be performed before, during and/or after the perfusion.

The method can also optionally comprise removal of cells, in particular the cell aggregate or cell aggregates, from the substrate, in particular after the perfusion and, if applicable, microscopic examination. If the cell aggregates are not removed as a whole, the cells can optionally be lysed and the resulting cell suspension removed, for example sucked off. If the substrate, as shown in FIG. 1, has an opening closed with a lid, for example a lid in the form of a film, for example adhesive film, the lid can be taken off for removal so that cells can be removed directly from the chamber. In that case, the cell aggregate can optionally be removed as a whole, for example with a pipette. This is shown schematically in FIG. 10h.

It is understood that features mentioned in the previously described embodiments are not limited to these particular combinations and are also possible in any other combinations.

What is claimed is:

1. A method for culturing cells in a substrate, the method comprising:
    introducing cells into a chamber of the substrate, the substrate having a microfluidic structure and comprising a first microfluidic channel and a second microfluidic channel connected to the chamber, the chamber having at least one side wall, a continuous planar bottom, and a top, wherein the top covers the chamber;
    tilting the substrate to a tilted orientation such that the cells accumulate in an arrangement on a side wall of the chamber;
    holding the substrate in the tilted orientation so that the cells form a three-dimensional cell aggregate, such that the cells grow together approximately in the arrangement in which they have accumulated on the side wall of the chamber;
    tilting the substrate back to a non-tilted orientation following formation of the three-dimensional cell aggregate; and
    perfusing the three-dimensional cell aggregate in the chamber by transporting liquid into and/or out of the chamber via the first microfluidic channel and/or the second microfluidic channel.

2. The method according to claim 1, wherein the substrate comprises a plurality of chambers and cells are introduced into each of the plurality of chambers before tilting, so that by the tilting and holding of the substrate, a distinct three-dimensional cell aggregate is formed simultaneously in each of the plurality of chambers.

3. The method according to claim 2, wherein the method further comprises perfusing a plurality or all of the cell aggregates.

4. The method according to claim 3, wherein the cell aggregates are perfused independently.

5. The method according to claim 1, wherein the substrate is tilted from an arrangement in which the continuous planar bottom of the chamber is arranged substantially horizontally by an angle of 20° to 45°.

6. The method according to claim 5, wherein the bottom of the chamber is arranged substantially horizontally by an angle of 30° to 40°.

7. The method according to claim 6, wherein the continuous planar bottom of the chamber is arranged substantially horizontally by an angle of 35°.

8. The method according to claim 1, wherein the holding of the substrate is for 4 to 26 hours, 6 to 25 hours, 8 to 24 hours, 10 to 23 hours, 12 to 22 hours, 14 to 21 hours, 16 to 20 hours, 17 to 19 hours, or 18 hours.

9. The method according to claim 1, wherein the perfusing is performed by means of one or a plurality of pumps and/or passively transporting the liquid into and/or out of the chamber.

10. The method according to claim 9, wherein the passively transporting the liquid into and/or out of the chamber is by means of gravity.

11. The method according to claim 1, wherein the perfusing comprises passively transporting the liquid into and/or out of the chamber, wherein the substrate is tilted to transport the liquid.

12. The method according to claim 1, wherein the perfusing comprises the three-dimensional cell aggregate being placed in a liquid stream or superperfusion of the three-dimensional cell aggregate.

13. The method according to claim 1, further comprising:
    performing microscopic examination of the three-dimensional cell aggregate while the three-dimensional cell aggregate is disposed on the continuous planar bottom in the non-tilted orientation in the chamber.

14. The method according to claim 13, wherein the microscopic examination of the three-dimensional cell aggregate in the chamber is through the continuous planar bottom of the chamber.

15. The method according to claim 1, wherein:
    the continuous planar bottom is a continuous planar cell-repellent bottom;
    the substrate comprises an opening in the top above the chamber, wherein the opening is closed with a lid during the formation of the three-dimensional cell aggregate; and
    the method further comprises removing the cell aggregates from the substrate through the opening, wherein the lid is taken off for the removal and the cell aggregates are subsequently removed directly from the chamber through the opening.

16. The method according to claim 15, wherein the lid comprises a film.

17. The method according to claim 15, wherein the opening is closed with the lid during perfusion.

18. The method according to claim 1, wherein the perfusing of the three-dimensional cell aggregate in the chamber is performed during and/or after the substrate tilting back to the non-tilted orientation.

19. The method according to claim 18, wherein the tilting back is tilting back to an initial position from which the substrate was tilted into the tilted orientation.

* * * * *